United States Patent [19]
Bedford et al.

[11] Patent Number: 5,624,678
[45] Date of Patent: Apr. 29, 1997

[54] METHOD AND COMPOSITION FOR TREATMENT AND/OR PROPHYLAXIS OF COCCIDIOSIS

[75] Inventors: Michael R. Bedford; Andrew J. Morgan, both of Marlborough; Michael A. Taylor; Janet Catchpole, both of Addlestone, all of United Kingdom

[73] Assignees: Finnfeeds International Limited, Wiltshire, Great Britain; Minister of Agriculture, Fisheries and Food, London, Great Britain

[21] Appl. No.: 435,946

[22] Filed: May 10, 1995

[30] Foreign Application Priority Data

May 10, 1994 [GB] United Kingdom .................. 9409336

[51] Int. Cl.$^6$ ...................................................... A23K 1/165
[52] U.S. Cl. ............................... 424/442; 424/438; 426/2; 426/807
[58] Field of Search ................................ 424/442, 438; 426/2, 807

[56] References Cited

U.S. PATENT DOCUMENTS

| | | | |
|---|---|---|---|
| 3,683,069 | 8/1972 | Hooreman | 424/94.63 |
| 3,932,619 | 1/1976 | Brannon et al. | 424/120 |
| 5,135,746 | 8/1992 | Matsuno et al. | 514/53 |
| 5,314,692 | 5/1994 | Haarasilta et al. | 424/94.2 |
| 5,429,828 | 7/1995 | Fodge et al. | 426/18 |

FOREIGN PATENT DOCUMENTS

| | | |
|---|---|---|
| 58-043922 | 3/1983 | Japan . |
| 4182433 | 6/1992 | Japan . |
| 1156010 | 6/1969 | United Kingdom . |
| 9301800 | 2/1993 | WIPO . |
| 9313786 | 7/1993 | WIPO . |

*Primary Examiner*—D. Gabrielle Phelan
*Attorney, Agent, or Firm*—Watson Cole Stevens Davis, P.L.L.C.

[57] ABSTRACT

The present invention provides a method of use, and a composition, of a carbohydrase and/or a protease for the manufacture of an agent for the treatment and/or prophylaxis of coccidiosis. The agent can be in the form of a cereal-based animal feed. The carbohydrase may be a polysaccharidase such as a xylanase or a cellulase e.g., β-glucanase. The agent may include conventional non-enzymic anticoccidial agents.

31 Claims, No Drawings

METHOD AND COMPOSITION FOR TREATMENT AND/OR PROPHYLAXIS OF COCCIDIOSIS

The present invention relates to the use of certain enzymes for the manufacture of an agent for the treatment and/or prophylaxis of coccidiosis.

Coccidiosis is a common cause of disease in intensively-reared farm livestock, particularly in poultry. Coccidiosis is caused by a protozoa, a single-celled parasite, of the sub-phylum Apicomplexa. Many of the species that cause the disease in domestic animals belong to the genus Eimeria. The parasites multiply in the epithelium of the intestine. In chickens, seven species of Eimeria have been described, five of which are considered to be pathogenic. These are *E. acervulina, E. maxima, E. necratrix, E. tenella* and *E. brunetti.*

Coccidia are ubiquitous organisms and are generally endemic wherever chickens are raised. Outbreaks of disease can vary from severe to very mild infections. Like many parasitic protozoa, the life cycle of the Eimeria is relatively complex. Sexual and asexual multiplication occurs within the chickens' intestines. During this process of multiplication and development of the parasite, the host tissue is destroyed which leads to the various clinical manifestations observed in outbreaks of coccidiosis. The oocysts produced and excreted develop further outside the host where they may undergo further development and infect other chickens. Oocysts can in fact survive outside the host for a long period of time which enables them to infect subsequent crops of birds. They may also be spread between flocks by other agents including people, pets, insects, rodents, dust and other birds.

Sporulated oocysts contain four sporocysts, each containing two sporozoites. These sporozoites are released by mechanical and enzymatical action in the digestive tract of the chicken. This enables them to invade the epithelial cells in the intestine or caeca depending on the Eimera species involved.

Although there are differences in pathogenicity between species and strains of Eimeria, the overall symptoms may be one or more of the following: bloody droppings, high mortality, general lethargy, emaciation, a marked drop in teed consumption, diarrhoea and a drop in egg production. It has been estimated that coccidiosis is probably responsible for around 6–10% of unwanted mortality among poultry flocks. Additionally, subclinical disease increases Feed Conversion Ratios and lowers performance. Accordingly, the economic consequences of this disease are considerable.

Various methods have been tried in an attempt to combat coccidiosis. Attempts have been made to control the disease through management strategies based on high standards of hygiene together with the use of chemical disinfectants in the environment of the poultry. However, even under extremely high hygienic conditions, it has not been found possible to eradicate coccidiosis although such measures were found to lower the initial infection pressure in a poultry house. Both live and attenuated vaccines have been investigated as methods of control, but these have only recently become available and are relatively expensive.

At present, coccidiosis in poultry is routinely controlled by the use of preventive anticoccidial drug programmes. Such programmes attempt to restrict coccidial infections thus limiting the effects of subclinical outbreaks of disease. This is usually accomplished by the continuous inclusion of anticoccidial agents in the feed from early in the life of the flock until close to slaughter for broiler birds or by controlled withdrawal for layers. When first developed, such agents were used individually. This often resulted in strains of parasites developing drug-resistance. It is presently attempted to control coccidiosis by the continual introduction of new drugs or by the use of drug programmes involving rotational use of anticoccidial agents of different biochemical structures either during the grow-out period (shuttle programmes) or at frequent intervals (rotation programmes). In spite of the routine use of anticoccidial agents in poultry feeds, subclinical coccidiosis is still found on the majority of poultry farms. Further the use of anticoccidial drugs adds significantly to the costs of poultry production. It would be an advantage if the amounts of such anticoccidial agents which presently have to be included in feeds to control coccidiosis could be reduced, or even eliminated entirely.

Accordingly, one object of the present invention is to provide a fresh class of compounds which can be used for the treatment and/or prophylaxis of coccidiosis.

Accordingly, the present invention provides the use of an enzyme selected from a carbohydrase and/or a protease for the manufacture of an agent for the treatment and/or prophylaxis of coccidiosis.

It has most surprisingly been found that the inclusion of a carbohydrase and/or a protease in the diet of an animal has the effect of treating or preventing coccidiosis. If such an enzyme is included in the diet of an animal, then the amounts of anticoccidial drugs which have previously been routinely incorporated in its diet can be reduced or in some cases omitted entirely. This enables considerable economic savings to be achieved in view of the relative expense of anticoccidial drugs.

When omitting anticoccidial drugs from an animal's diet, there are several potential further benefits. Thus, it has previously been necessary to withdraw anticoccidial drugs from the animal's diet for a certain period of time prior to slaughter. This ensures that the meat is relatively free from such drugs and so fit for human consumption. In contrast, if anticoccidial drugs are omitted entirely from the animal's normal diet, as may be achieved in accordance with the present invention, then the animal can be slaughtered at any age rather than after a certain withdrawal period. This gives the farmer improved flexibility, and removes the risk of poultry becoming infected shortly prior to slaughter. Further, anticoccidial drug-residue free meat and eggs can be guaranteed. Such meat and eggs have a market advantage as compared to products which cannot support such a guarantee.

Even if the enzyme added to the animal's diet only enables the amount of anticoccidial drugs to be reduced, then the overall cost of controlling coccidiosis will be reduced. Synergy or potentiation may extend the useful life of the anticoccidial drug.

In a further aspect of the present invention, one or more of a carbohydrase and/or a protease may be included in the diet of an animal together with a conventional concentration of anticoccidial drugs. It has been found that this combination gives rise to a particularly advantageous synergy in that the resulting anticoccidial effect is greater than the mere addition of the individual effects of the enzyme(s) and anticoccidial drugs used separately.

The enzyme can be formulated as a pre-mix together with any other enzymes to be included in the feed. The pre-mix can be added to the raw materials before feed manufacture, during feed manufacture or as a final step once the feed is otherwise ready for use. It is also possible to add the enzyme directly as a liquid to a feed material pre-formed as pellets or as a mash.

It is also possible to include the enzyme in the animal's diet by incorporating it into a second (and different) feed or drinking water which the animal also has access to. Accordingly, it is not essential that the enzyme is incorporated into the feed itself, although such incorporation forms a particularly preferred aspect of the present invention.

If the enzyme is incorporated into the feed, then this preferably comprises at least 25% by weight of a cereal, and more preferably at least 35% by weight of the cereal. The cereal can be any one or more of wheat, rye, triticale, barley, oats, sorghum, rice and maize. It is particularly preferred that the cereal is wheat.

Although the cereal component of a cereal-based diet constitutes a source of protein, it is usually necessary to include sources of supplementary protein in the diet such as those derived from fishmeal, meatmeal or vegetables. These sources of supplementary protein can constitute up to 50% by weight of the animal feed. Sources of vegetable proteins include at least one of full fat soybeans, rapeseed, canola, soybean meal, rapeseed meal and canola meal.

If the enzyme is incorporated into the feed, then this is preferably done in a relative amount of 0.00001–10 g of the enzyme protein per kilo of the feed; more preferably 0.0001–1 g/kg; and most preferably 0.001–0.1 g/kg.

In the case that the enzyme used is a carbohydrase, then this is preferably a polysaccharidase such as a xylanase, a cellulase, an $\alpha$-amylase or a pectinase. A preferred cellulase is $\beta$-glucanase.

If the polysaccharidase is a xylanase, then this may be obtained from a fungal source such as Trichoderma, Aspergillus, Humicola or Neocallimastix. It is particularly preferred that the xylanase is the low pI xylanase and/or the high pI xylanase obtainable from *Trichoderma longibrachiatum* such as described in WO 92/06209. Alternatively, the xylanase can also be obtained from a bacterium such as Bacillus, Streptomyces, Clostridium or Ruminococcus. It is also possible that the xylanase may be obtained from a host which has been subjected to genetic manipulation such as by the inclusion of an appropriate gene within a host bacterial or fungal strain.

In the case that the enzyme used is a protease, then this may be a subtilisin derived from the genus Bacillus. Such subtilisins are for example described in detail in U.S. Pat. No. 4,760,025.

According to one preferred aspect of the present invention, the therapeutic agent does not include any non-enzymic anticoccidial agent. However, if such an agent is present, for instance to counter an outbreak of coccidiosis, then a conventional anticoccidial agent such as salinomycin, monensin, narasin, lasalocid, nicarbazin, maduramycin, nicarbazin and narasin in combination, diclazuril, dinitolmide, halofuginone, robenidine, amprolium or clopidol can be used. Such non-enzymic anticoccidial agents can be included in an animal feed preferably in an amount of 0–100 ppm, and more preferably 0–50 ppm. The latter amount in particular is well below the normal amounts of 50–200 ppm used fiber the majority of anticoccidial agents included in animal feeds.

This provides one of the advantages of the present invention of economic savings resulting from the use of lower amounts than is conventional of such relatively costly anticoccidial agents.

As mentioned above, it is preferred that the agent provided by the present invention is in the form of an animal feed. A suitable feed can be obtained by preparing a pre-mix of the carbohydrase and/or protease on a cereal carrier, and then adding an appropriate amount, e.g. 1 part by weight, of this pre-mix to 1000 parts by weight of a conventional animal feed.

Coccidiosis can be treated or prevented in accordance with the present invention in a variety of livestock. Thus, the enzyme of the present invention can be provided in the form of an agent, such as an animal feed, to livestock such as chicken, turkeys, geese, ducks, pigs, sheep or cattle. It is however particularly preferred that the agent is administered to broiler chickens.

The present invention is further explained by way of the following Examples.

EXAMPLE 1

Four separate groups (A–D), each consisting of ten female Lohmann Brown chicks, were fed the following maize/wheat-based diet for their first twelve days of life:

| Maize/wheat-based diet | |
|---|---|
| Wheat | 25% by weight |
| Maize | 42% by weight |
| Soybean meal | 20% by weight |
| Fishmeal | 10% by weight |
| Vitamin and Mineral Mixture | 3% by weight |

Each of the groups were then fed the following wheat-based diet for the days 13–21:

| Wheat-based diet | |
|---|---|
| Wheat | 67% by weight |
| Soybean meal | 20% by weight |
| Fishmeal | 10% by weight |
| Vitamin and Mineral mixture | 3% by weight |

The diet of the chicks in the groups C and D was supplemented by an enzyme mix including xylanase obtained from *Trichoderma Longibrachiatum* and $\beta$-glucanase also obtained from *Trichoderma Longibrachiatum*. Thus, a pre-mix containing crude xylanase and crude $\beta$-glucanase was prepared and coated on a cereal carrier. This was then added to the above wheat-based feed such that the resulting feeds comprised about 0.0025 g of xylanase protein and about 0.005 g of $\beta$-glucanase protein per kg of feed. The diets fed to the chicks in groups A and B were not supplemented with enzymes.

The chicks in groups B and D were infected with oocysts on day 14. This infection took the form of 5000 *E. tenella* and 50000 *E. acervulina* oocysts per chick. The chicks in groups A and C were not infected.

On day 21, seven days alter infection, the chicks were killed and body weight gain and lesion scoring according to the Johnson and Reid system (Exp. Parasitol. (1970) Vol. 28, pp 30–36) in both the duodenum and caecae were undertaken. The results obtained are set out in the following Table 1:

TABLE 1

| Group | Enzyme | Infection | Average Body Weight gain (g) | Lesion Score |
|---|---|---|---|---|
| A | – | – | 89.2 | 0.00 |
| B | – | + | 42.4 | 3.78 |
| C | + | – | 91.4 | 0.00 |
| D | + | + | 63.5 | 3.00 |

It can be understood from the above results that coccidial infection in the group B leads to a significant loss in average body weight gain and a disadvantageous increase in lesions as compared to the control group A. On the other hand, it is clear that when the wheat-based diet of the chicks is supplemented by enzymes in the case of group D, then the effects of coccidial infection are markedly reduced. In particular, the average body weight gain for the chicks in group D is significantly greater than for the chicks in group B. Further, the lesion score for the chicks in group D was lower than the lesion score for the chicks in group B.

EXAMPLE 2

Four groups (E-H), each consisting of twenty Ross male broiler chicks were fed the wheat-based diet set out in the above Example 1 for their first twenty-eight days. The diets of the chicks in groups F and H were supplemented with xylanase obtained from *Trichoderma Longibrachiatum*. Thus a pre-mix containing crude xylanase was prepared and coated on a cereal carrier. This was then added to the above wheat-based feed such that the resulting feeds comprised about 0.0025 g of xylanase protein per kg of feed. The diets fed to the chicks in groups E and G were not supplemented with xylanase.

The chicks in groups G and H were infected with oocysts on day 14 in the same manner as the groups B and D were infected in the above Example 1.

On day 21, seven days after the infection was introduced, the average body weight gain, average feed intake and feed conversion ratio of the chicks in each group were measured. In addition, 10 chicks from each group were killed and their intestinal viscosity measured. These chicks were also subjected to lesion scoring according to the Johnson and Reid system in both the duodenum and caecae. The results are set out in Table 2 below:

other hand, the body weight gain for the chicks in group H picked up markedly in the period 7-14 days after infection as can be seen from the results in Table 3.

From these Tables, it is also clear that there is a negative effect on the feed conversion ratio (FCR) due to coccidial infection. It should be mentioned that the FCR of a feed is the ratio of the amount of feed consumed relative to the weight gain of the animal. A low FCR indicates that a given amount of feed results in a growing animal gaining proportionately more weight. This means that the animal is able to utilise the feed more efficiently. Enzyme addition numerically has a significant impact on the FCR results in Table 2. Thus, the FCR is improved by about 19% in the case of infected birds whose diets are supplemented by the enzymes. In comparison, for birds which are not infected, the FCR of the chicks whose diets are supplemented by enzymes improves only by 8.5% compared to the chicks in the group whose diets are not so supplemented.

Turning to the results set out in Table 3, it will be seen that body weight gain was substantially increased by enzyme addition in the infected group H as compared to the group G which were not provided with enzyme supplements. This is a most unexpected but advantageous finding. In contrast, it can be seen by comparing the results for groups E and F in Table 3 that the addition of enzyme in the absence of infection has no significant effect.

The FCR data set out in Table 3 apparently shows the best value for the group G. However, this is misleading because the chicks in this group grow so slowly that they will not meet the required end body weight after the usual growing period, and the economic loss caused by this offsets any advantage in improved feed conversion.

TABLE 2

| Group | Enzyme | Infection | Average Body Weight Gain (g) | Average Feed Intake (g) | Feed conversion Ratio | Lesion Score | Viscosity (Pa · s) |
|---|---|---|---|---|---|---|---|
| E | − | − | 318 | 670 | 2.11 | 0 | 0.0184 |
| F | + | − | 347 | 670 | 1.93 | 0 | 0.00625 |
| G | − | + | 242 | 610 | 2.52 | 1.9 | 0.00607 |
| H | + | + | 244 | 500 | 2.05 | 2 | 0.00266 |

The ten remaining chicks in each of the groups E-H were fed for a further seven days, that is for a period ending 14 days after infection. These chicks were then assessed for their average body weight gain, average feed intake and feed conversion ratio. The results obtained are set out in the following Table 3:

EXAMPLE 3

Ross male broilers were fed the wheat-based feed set out in the above Example 1 for their first 12 days. At Day 12, the birds were randomised by weight into eight groups each containing 20 broilers. These eight groups "T"–"L" were

TABLE 3

| Group | Enzyme | Infection | Average Body Weight Gain (g) | Average Feed Intake (g) | Feed Conversion Ratio |
|---|---|---|---|---|---|
| E | − | − | 430 | 920 | 2.14 |
| F | + | − | 426 | 880 | 2.06 |
| G | − | + | 396 | 740 | 1.87 |
| H | + | + | 467 | 940 | 2.01 |

The results set out in Table 2 above indicate that average body weight gain was significantly depressed by coccidial infection with or without enzyme supplementation. On the provided with feeds in accordance with the following Table 4:

TABLE 4

| Group | Feed |
| --- | --- |
| I– | Wheat alone |
| J– | Wheat + 5 ppm of Cygro |
| K– | Wheat + enzyme |
| L– | Wheat + enzyme + 5 ppm of Cygro |
| I+ | Wheat alone |
| J+ | Wheat + 5 ppm of Cygro |
| K+ | Wheat + enzyme |
| L+ | Wheat + enzyme + 5 ppm of Cygro |

In the above Table 4, the feed provided to Group I is the initial wheat-based feed. The feeds provided to Groups J and L are each supplemented with 5 ppm of Maduramycin (the recommended level of inclusion) which is an anti-coccidial ionophore marketed as Cygro by Cyanamid. The enzyme which is included in each of the feeds provided to Groups K and L is a xylanase obtained from *Trichoderma longibrachiatum*. This is added as a pre-mix, which contains 0.375% of xylanase protein, to the feed in an amount of 0.6 g of the pre-mix per kg of the feed.

At Day 14, the four "+" groups were orally infected with 50,000 oocysts of *E. acervulina* and 5,000 oocysts of *E. tenella*. Feed conversion ratios (for some groups) and lesion scores were measured. The results for the measurement of the feed conversion ratios during the trial are set out in the following Table 5:

TABLE 5

| Group | Day 0 to 7 | Days 7 to 14 | Days 0 to 14 |
| --- | --- | --- | --- |
| I– | 2.27 | 2.85 | 2.49 |
| K– | 2.49 | 2.94 | 2.67 |
| I+ | 2.63 | 2.48 | 2.56 |
| K+ | 2.51 | 2.11 | 2.50 |

From the above results, it will be seen that the inclusion of the enzyme in the feed provided to Group K+ improved the feed conversion ratio over the critical 7 day period following infection compared to Group I+ fed the unsupplemented wheat diet. This effect was sustained throughout the duration of the trial.

Seven days after infection, 10 birds from each group were killed and examined for lesions caused by *E. acervulina* and *E. tenella* according to the method of Johnson & Reid. The results obtained are set out in the following Table 6:

TABLE 6

| Group | E. acervulina | E. tenella |
| --- | --- | --- |
| I– | 0 | 0 |
| J– | 0 | 0 |
| K– | 0 | 0 |
| L– | 0 | 0 |
| I+ | 2.5 | 2.6 |
| J+ | 2.2 | 2.2 |
| K+ | 2.1 | 2.8 |
| L+ | 2.0 | 1.7 |

From the results set out above, it can be seen that lesion scores for *E. acervulina* were significantly lower for groups whose feeds were supplemented with the enzyme as compared to the closest comparable control groups. The inclusion of the enzyme in the feeds improved the lesion scores and also gave rise to a further improvement when used in combination with the anti-coccidial agent. The lesion scores caused by *E. tenella* did not improve on enzyme supplementation alone compared to the unsupplemented wheat diet. On the other hand, the presence of the enzyme did significantly improve the performance of the anti-coccidial agent as can be seen from a comparison between Groups J+ and L+.

EXAMPLE 4

Ross male broilers were fed the wheat-based feed set out in the above Example 1 for their first 12 days. At Day 12, the birds were randomized by weight into two groups each containing 66 broilers. These two Groups "M" and "N" were provided with feeds as follows.

The feed of Group N was the initial wheat-based diet without any supplementation. The feed of Group M was the same feed supplemented with a xylanase enzyme obtained from *Trichoderma longibrachiatum*. This enzyme was added as a pre-mix containing 0.187% of xylanase protein to the feed in an amount of 1 g of the pre-mix per kg of the feed. The pre-mix also included a protease obtained from Bacillus sp. This is present in the pre-mix in an amount of 0.06% of protease protein.

At Day 14, the two groups were orally infected with 30,000 oocysts of *E. acervulina*, 15,000 oocysts of *E. maxima* and 3,000 oocysts of *E. tenella*. Seven days after infection, birds front each group were killed and examined for lesions caused by *E. acervulina*, *E. maxima* and *E. tenella* according to the method of Johnson & Reid. The results obtained are illustrated in the following Table 7:

TABLE 7

| Diet | Lesion Score E. acervulina | Lesion Score E. maxima | Lesion Score E. tenella |
| --- | --- | --- | --- |
| Group N | 1.8 | 0.8 | 2.5 |
| Group M | 1.8 | 0.6 | 1.7 |

From these results, it can be seen that lesion scores were reduced in Group M fed the enzyme supplemented feeds in the case of lesions caused by both *E. maxima* and *E. tenella*.

The effect demonstrated above of treating coccidiosis in the case of wheat-based diets can also be obtained in feeds based on rye, triticale, barley, oats, sorghum, rice or maize. Further, similar results can be obtained when feeds incorporating enzyme supplementation in accordance with the present invention are fed to other animals infected or infectable by coccidiosis such as turkeys, geese, ducks, pigs, sheep and cattle.

The dosage of the enzyme is typically any suitable therapeutic amount, for treatment and/or prophylaxis (prevention) of coccidiosis, added to animal feed. The feed may be food, water or inert (but edible) material. The dosage may be increased, decreased and/or repeated as appropriate for the animal, depending on potential or actual infection, animal body weight, animal eating habits and other feed ingredients.

The enzyme may be fed to an animal having, or under a threat of having, coccidiosis. A threat of coccidiosis includes (i) animals where an outbreak of coccidiosis in their group, e.g., herd or flock, has been detected or (ii) animals for which due to the nature of how the animals are raised, e.g., being raised in close proximity to each other, it is highly possible for them to contract coccidiosis. The enzyme may be fed during the majority, or preferably throughout, the life of the animal to prevent coccidiosis.

The present invention also has the substantial benefit that use of the enzyme in animal feed together with the above-mentioned non-enzymic anticoccidial agent allows much lower levels of these non-enzymic anticoccidal agents to be employed to treat coccidiosis. This results from a synergy between the enzyme and non-enzymic agents. These low levels are beneficial because the non-enzymic agents are expensive.

In general, when employed with the enzymes according to the present invention, the non-enzymic agents may be employed at about 30 to about 60 percent, preferably about 40 to about 60 percent, or most preferably about 50 percent, of their normally recommended dosage level.

Normally, the majority of non-enzymic anti-coccidal agents are employed in the feed at levels of 50–200 ppm. Thus, when employed with enzymes according to the present invention, such non-enzymic agents may be employed at levels of 0–100 ppm, more preferably 0 to 50 ppm and most preferably about 0.5 to about 40 ppm (or even about 0.5 to about 25 ppm where therapeutic).

The following non-enzymic agents are normally employed at low-levels in animal feed: diclazuril, 1 ppm; halofuginone, 3 ppm; and maduramycin, 5 ppm. If these non-enzymic agents are employed with the enzymes, according to the present invention, then their dosages could be reduced. For example, a 50% reduction would result in dosages of 0.5 ppm, 1.5 ppm and 2.5 ppm, respectively.

We claim:

1. A method for the treatment and/or prophylaxis of coccidiosis in an animal comprising the step of:
   administering to the animal an agent comprising
      a therapeutically effective amount of a carbohydrase, as a therapeutically active agent for treatment and/or prophylaxis of coccidiosis.

2. The method according to claim 1, wherein the agent is in the form of an animal feed.

3. The method according to claim 2, wherein the animal feed comprises at least 25% by weight of a cereal.

4. The method according to claim 3, wherein the animal feed comprises at least 35% by weight of the cereal.

5. The method according to claim 3, wherein the cereal is at least one of wheat, rye, triticale, barley, oats, sorghum, rice and maize.

6. The method according to claim 5, wherein the cereal is wheat.

7. The method according to claim 5, wherein the cereal is at least one of sorghum, rice and maize.

8. The method according to claim 2, wherein the feed further comprises a supplemental source of protein.

9. The method according to claim 8, wherein the supplemental source of protein is fishmeal, meatmeal or a vegetable protein.

10. The method according to claim 9, wherein the supplemental source of vegetable protein is at least one of full fat soybeans, rapeseed, canola, soybean meal, rapeseed meal and canola meal.

11. The method according of claim 2, wherein the animal feed comprises 0.00001–10 g/kg of the carbohydrase protein.

12. The method according to claim 11, wherein the animal feed comprises 0.0001–1 g/kg of the carbohydrase protein.

13. The method according to claim 12, wherein the animal feed comprises 0.001–0.1 g/kg of the carbohydrase protein.

14. The method according to claim 1, wherein the carbohydrase is one or more polysaccharidases.

15. The method according to claim 14, wherein the polysaccharidase is xylanase.

16. The method according to claim 15, wherein the xylanase is obtained from a fungus.

17. The method according to claim 16, wherein the fungus is Trichoderma, Aspergillus, Humicola or Neocallimastix.

18. The method according to claim 15, wherein the xylanase is obtained from a bacterium.

19. The method according to claim 18, wherein the bacterium is Bacillus, Streptomyces, Clostridium or Ruminococcus.

20. The method according to claim 14, wherein the polysaccharidase is a cellulase.

21. The method according to claim 20, wherein the cellulase is a β-glucanase.

22. The method according to claim 14, wherein the polysaccharidase is an α-amylase or a pectinase.

23. The method according to claim 1, wherein the agent further comprises a non-enzymic anti-coccidial agent.

24. The method according to claim 23, wherein the non-enzymic anti-coccidial agent is salinomycin, monensin, naraisn, lasalocid, nicarbazin, nicarbazin and narasin in combination, diclazuril, dinitolmide, halofuginone, robenidine, maduramycin, amprolium or clopidol.

25. The method according to claim 23, wherein the agent is in the form of an animal teed and includes 0.5–40 ppm of the non-enzymic anti-coccidial agent.

26. The method according to claim 23, wherein the agent is in the form of an animal feed and includes the non-enzymic anti-coccidial agent in an amount of about 30 to about 60% of the normal recommended dosage of the non-enzymic agent for treatment and/or prophylaxis of coccidiosis.

27. The method according to claim 1, wherein the agent is adapted to be administered to livestock selected from a chicken, a turkey, a goose, a duck, a pig, a sheep or cattle.

28. The method according to claim 27, wherein the livestock is a broiler chicken.

29. The method according to claim 1, wherein the carbohydrase is administered to an animal infected with coccidiosis.

30. The method according to claim 1, wherein the carbohydrase is administered to a group of animals when an animal of the group is found to be infected with coccidiosis.

31. A composition for the treatment and/or prophylaxis of coccidiosis in an animal comprising:
   a therapeutically effective amount of carbohydrate,
      as a therapeutically active agent for the treatment and/or prophylaxis of coccidiosis,
   a carrier for the carbohydrase; and
   a non-enzymic anti-coccidial agent in an amount from about 30 to about 60 percent of the non-enzymic agent's normally recommended dosage for treatment and/or prophylaxis of coccidiosis.

* * * * *